(12) United States Patent
Yadav et al.

(10) Patent No.: US 10,675,151 B2
(45) Date of Patent: Jun. 9, 2020

(54) SUTURE PASSAGES FOR PROSTHESES

(71) Applicant: Howmedica Osteonics Corp., Mahwah, NJ (US)

(72) Inventors: Rajan Yadav, New Delhi (IN); David Viscardi, Glen Rock, NJ (US); Koustubh Rao, Haryana (IN); Nicholas Olson, Belleville, NJ (US); Roy Philip Splieth, Central Valley, NY (US)

(73) Assignee: Howmedica Osteonics Corp., Mahwah, NJ (US)

( * ) Notice: Subject to any disclaimer, the term of this patent is extended or adjusted under 35 U.S.C. 154(b) by 150 days.

(21) Appl. No.: 15/922,267

(22) Filed: Mar. 15, 2018

(65) Prior Publication Data

US 2018/0280146 A1 Oct. 4, 2018

Related U.S. Application Data

(60) Provisional application No. 62/478,963, filed on Mar. 30, 2017.

(51) Int. Cl.
*A61F 2/30* (2006.01)
*A61F 2/32* (2006.01)
(Continued)

(52) U.S. Cl.
CPC ...... *A61F 2/30771* (2013.01); *A61B 17/7233* (2013.01); *A61F 2/32* (2013.01); *A61F 2/40* (2013.01); *A61F 2/4059* (2013.01); *A61B 17/0482* (2013.01); *A61B 17/842* (2013.01); *A61F 2/4657* (2013.01); *A61F 2002/3082* (2013.01); *A61F 2002/30331* (2013.01); *A61F 2002/30574* (2013.01); *A61F 2002/30784* (2013.01); *A61F 2002/30795* (2013.01); *A61F 2002/30884* (2013.01);
(Continued)

(58) Field of Classification Search
CPC ...... A61F 2/40; A61F 2/32; A61F 2/30; A61F 2002/30777; A61F 2002/30784; A61F 2002/3082; A61F 2/30771
See application file for complete search history.

(56) References Cited

U.S. PATENT DOCUMENTS 6,277,123 B1 8/2001 Maroney et al.
6,283,999 B1 9/2001 Rockwood, Jr.
(Continued)

FOREIGN PATENT DOCUMENTS

WO 012376 A1 1/2001

*Primary Examiner* — Dinah Baria
(74) *Attorney, Agent, or Firm* — Lerner, David, Littenberg, Krumholz & Mentlik, LLP

(57) ABSTRACT

Disclosed herein are an implant with a suture passage and a method of attaching sutures to the same. The implant may include a suture pocket having a first pocket, a second pocket, and a suture hole disposed therebetween. The first pocket may have a first wall segment, the second pocket may have a second wall segment, and the suture hole may have a first sidewall segment extending from a first opening to a second opening. The first wall segment, the second wall segment, and the first sidewall segment may form a contiguous wall. A method of attaching a suture to the implant may include placing a tip of a suture needle on the first wall segment, sliding the suture needle into the first opening and pushing the suture needle through the suture hole.

16 Claims, 8 Drawing Sheets

(51) Int. Cl.
    *A61F 2/40*         (2006.01)
    *A61B 17/72*       (2006.01)
    A61F 2/46         (2006.01)
    A61B 17/84       (2006.01)
    A61B 17/04       (2006.01)

(52) U.S. Cl.
    CPC .................. *A61F 2002/4062* (2013.01); *A61F 2002/4066* (2013.01); *A61F 2002/4687* (2013.01)

(56) References Cited

U.S. PATENT DOCUMENTS

| | | |
|---|---|---|
| 6,558,425 B2 | 5/2003 | Rockwood, Jr. |
| 6,702,824 B2 | 3/2004 | Maroney et al. |
| 2006/0189987 A1 | 8/2006 | Orbay et al. |
| 2011/0009973 A1* | 1/2011 | Meyers ................ A61F 2/3607 623/20.32 |
| 2011/0130840 A1 | 6/2011 | Oskouei |

* cited by examiner

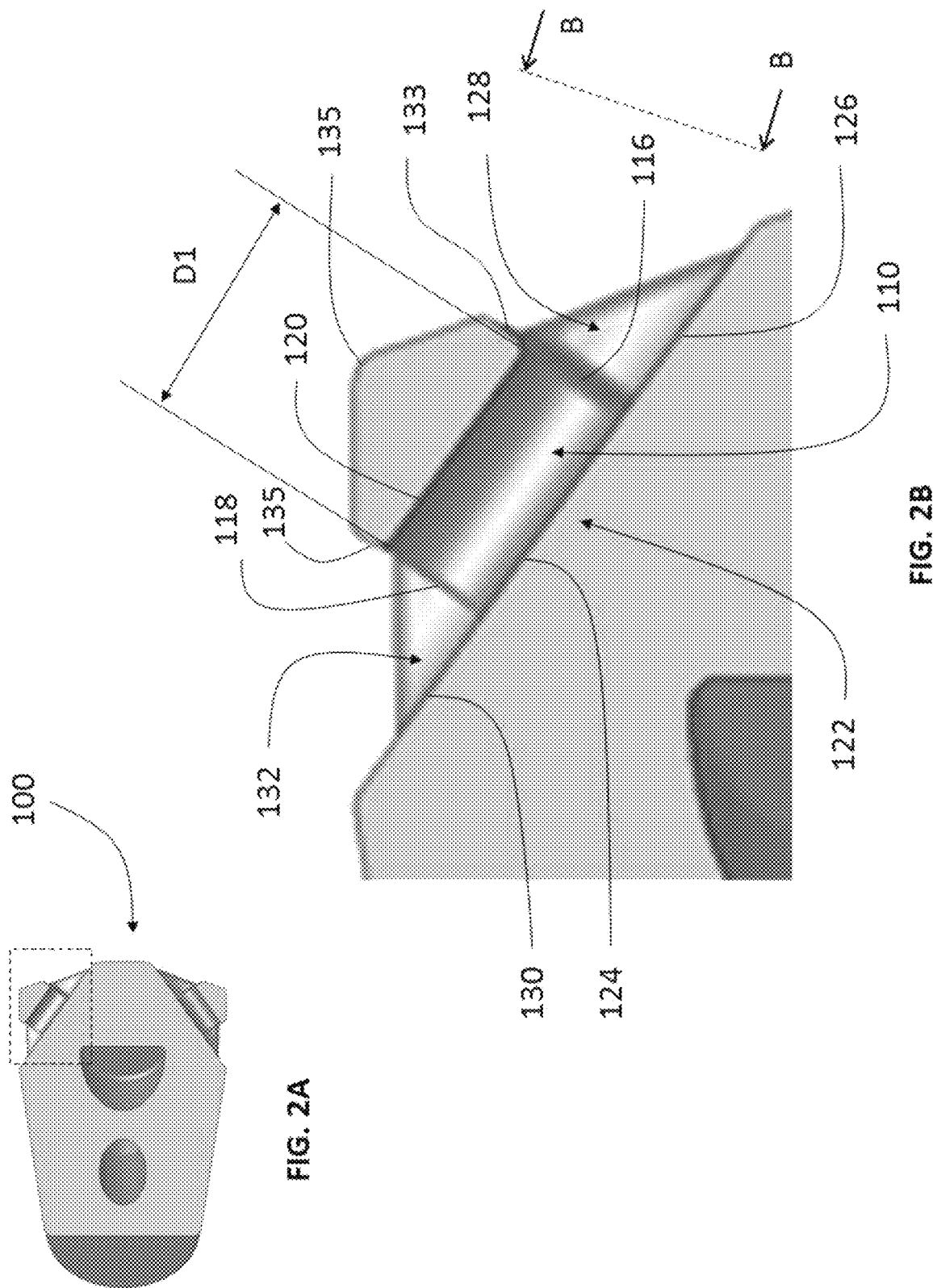

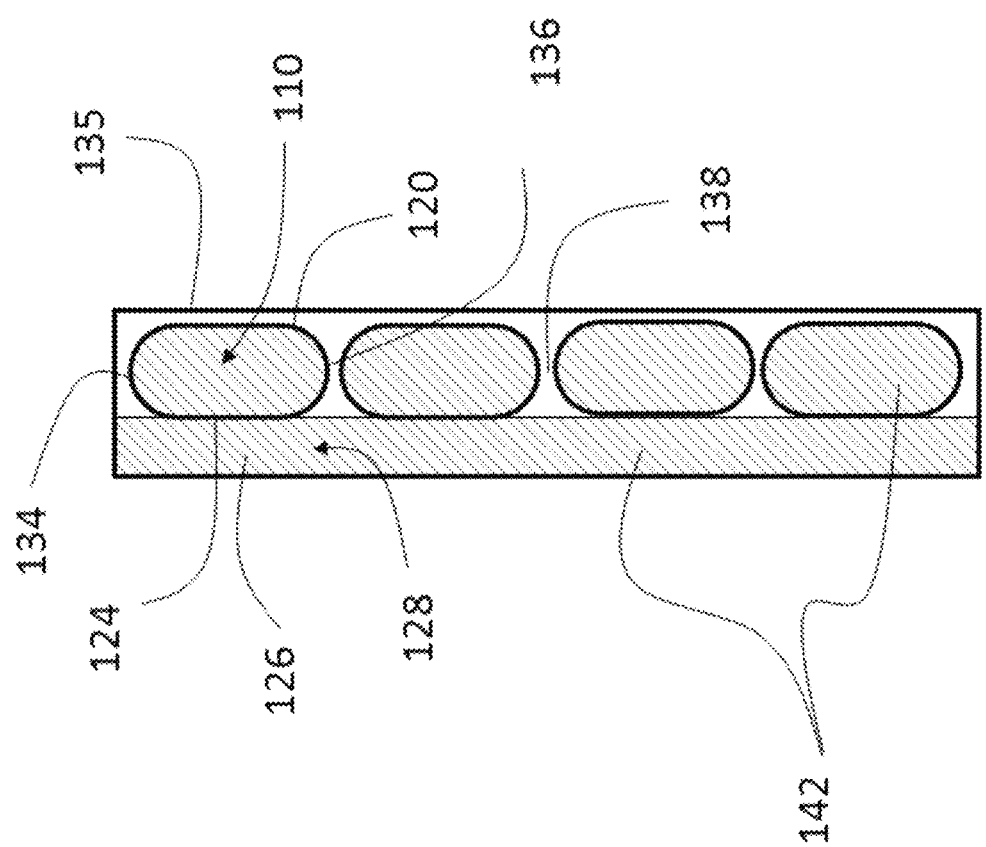

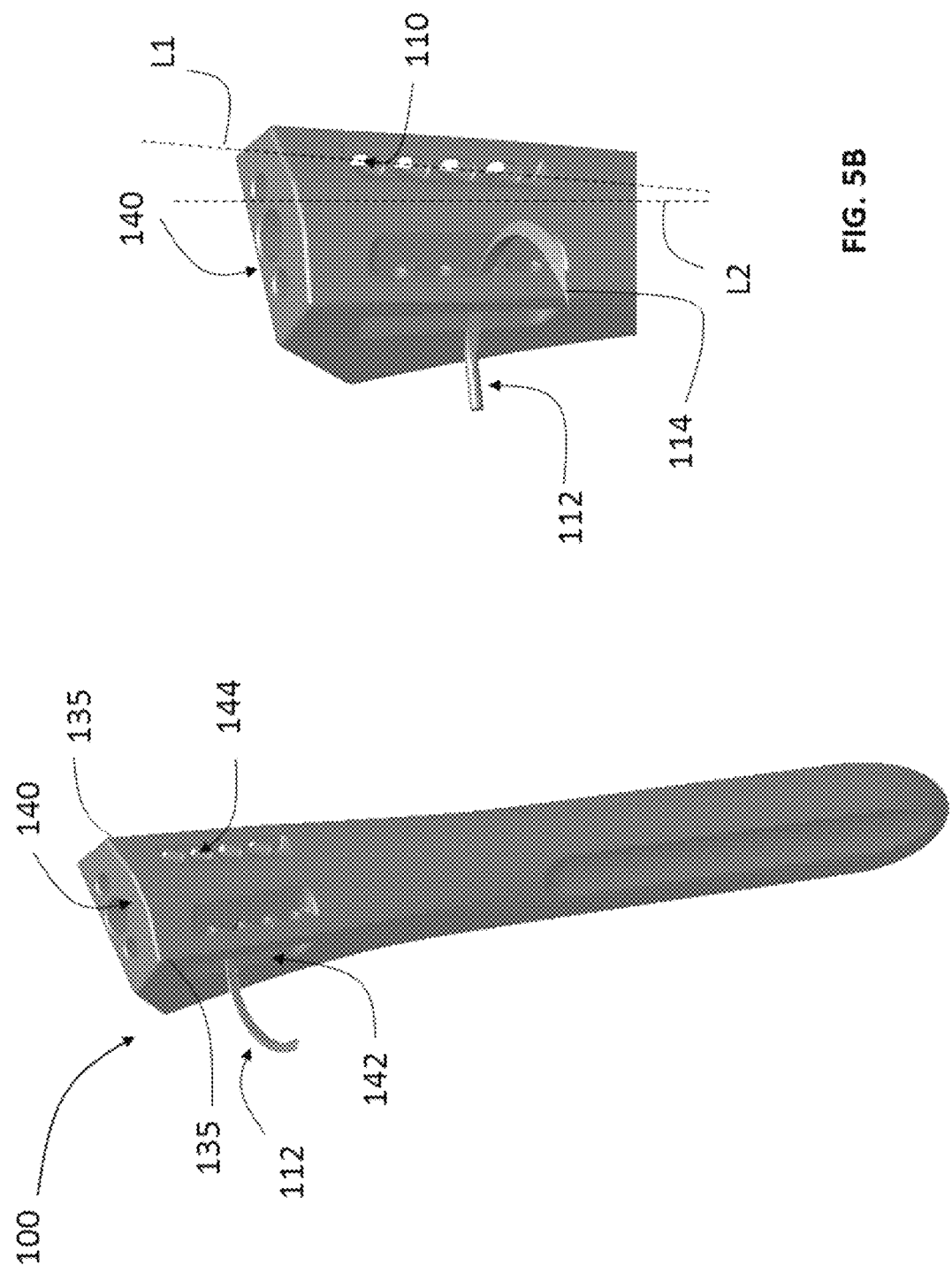

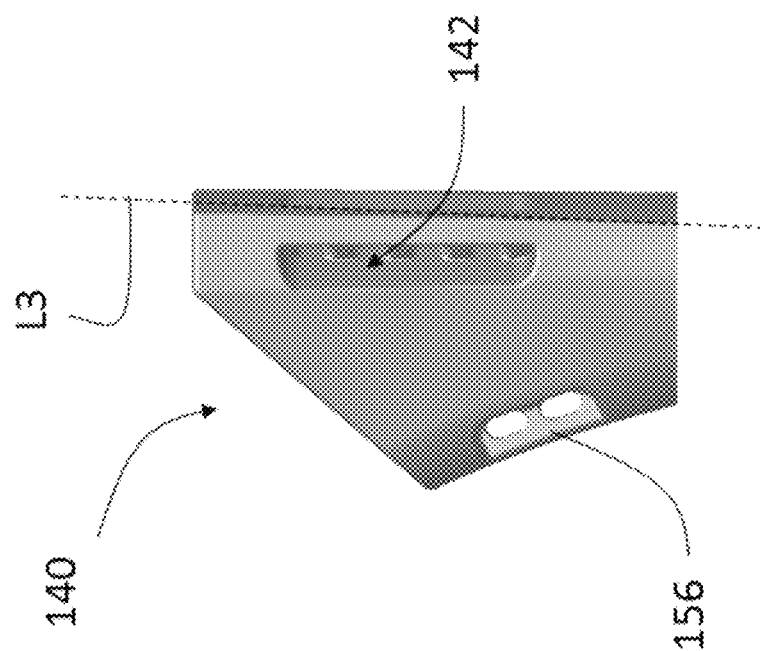
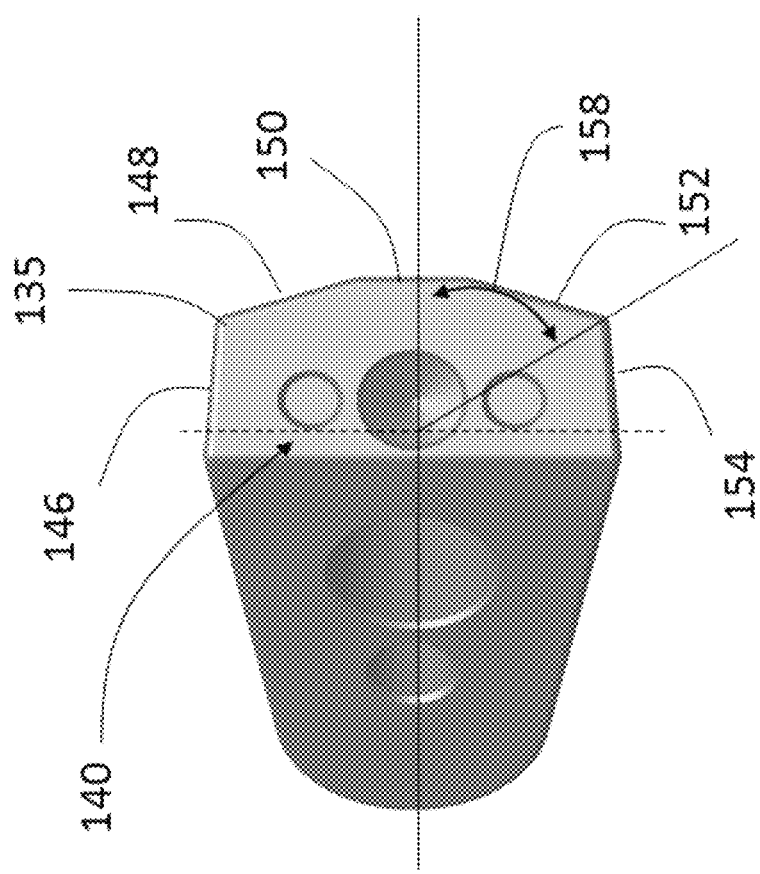
FIG. 6B
FIG. 6A

SUTURE PASSAGES FOR PROSTHESES

CROSS-REFERENCE TO RELATED APPLICATION

The present application claims the benefit of the filing date of U.S. Provisional Patent Application No. 62/478,963, filed on Mar. 30, 2017, the disclosure of which is hereby incorporated by reference.

FIELD OF THE INVENTION

The present invention relates to an implant with suture passages and a method of attaching sutures to the same and in particular an implant with suture pockets having suture holes and a method of attaching sutures to the same.

BACKGROUND OF THE INVENTION

Orthopedic surgeries may require implants to be attached to soft tissue and/or tuberosities by sutures. By way of example but not limitation, a fracture occurring in the proximal region of the humerus may require a shoulder prosthesis with multiple suture holes by which the prosthesis can be attached to the body. Attaching sutures to an implant requires a surgeon to successfully insert suture needles through these suture holes and therefore requires considerable time, skill and effort. Manipulation of suture needles through the narrow suture holes which are often located in tight, inaccessible locations can be challenging especially during surgery. A surgeon must precisely place a needle tip through the narrow suture hole for successful needle insertion, and repeat this step many times over to complete implant attachment to body.

Suture holes on implants such as a shoulder prosthesis are generally located on a fin or a flange to allow for soft tissue attachment. A vertical array of circular suture holes is provided on a fin to maximize visibility. Suture hole openings are generally flush with the fin surface. Therefore, suturing these holes will require precise location of the needle tip into the circular opening. If a surgeon misses the circular opening and contacts the needle tip to the fin surface, the surgeon must attempt again to successfully target the circular opening. Furthermore, a curved suture needle is generally used in such procedures and makes targeting the narrow suture hole openings more challenging and time-consuming for a surgeon. Furthermore, fins or flanges containing suture holes generally extend from the implant body into soft tissue or bone and will consequently require additional effort in positioning, and implanting the prosthesis.

Therefore, there exists a need for improved suture passages and a method for attaching sutures to an implant having the same.

BRIEF SUMMARY OF THE INVENTION

The present invention is for an implant with a novel suture passage and a method for attaching a suture to an implant having the same. The suture passage disclosed herein includes a suture hole with a first and a second suture pocket. Successful suture insertion into a suture hole of the present invention is not limited to placing a suture needle tip in the opening of a suture hole, instead a surgeon may insert a suture by placing a suture needle tip on a sidewall and then slide the needle into the suture hole. The sidewall extends beyond the suture hole and allows a suture needle tip to be guided into the suture hole.

A first aspect of the present invention is an implant having a suture hole and a suture pocket. In a first embodiment according to this first aspect, the suture hole is disposed between a first suture pocket and a second suture pocket. A first planar wall comprised of a first planar wall segment, a second planar wall segment and a first sidewall segment forms a planar wall to allow a suture needle to be slidably guided along the first and second planar sidewall segments and into the suture hole.

In a second embodiment according to this first aspect of the present invention, the suture hole includes an opposite second sidewall, wherein a first length defined by the second sidewall between a first and second opening of the suture hole is substantially the same or less than a chord length of a curved suture needle being disposed within the suture hole. The chord length is defined by the intersection of a plane containing the second sidewall when the curved suture needle is disposed in the suture hole.

In another embodiment according to this first aspect of the present invention, the chord length of the suture needle is less than the first length such that the suture needle can enter and exit the suture hole without contacting the first sidewall.

In another embodiment according to this first aspect of the present invention, the second sidewall segment is chamfered at the first and second openings to allow for suture needle entry and exit from the suture hole respectively. The first planar wall is tangential to a curved suture needle when the suture needle is disposed in the suture hole.

In yet another embodiment according to this first aspect of the present invention, the suture holes are oblong shaped to maximize insertion area. A plurality of suture holes is arranged vertically below each other between a first and second pocket. A vertical axis connecting the plurality of suture hole is offset to a vertical axis of the implant to maximize the number of suture holes. An implant according to this first aspect may include any of a shoulder or hip prostheses, wherein the first and second pockets may be aligned along a bicipital groove.

In a still yet another embodiment according to this first aspect of the present invention, a first wall segment, a second wall segment, and a first sidewall segment form a contiguous surface to allow a suture needle to be slidably guided along the first and second planar sidewall into the suture hole.

In a still yet another embodiment according to this first aspect of the present invention, a first wall segment, a second wall segment and a first sidewall segment form a contiguous surface to allow a suture needle to be slidably guided along the first and second sidewall segments and into the suture hole.

In a still yet another embodiment according to this first aspect, a suture hole is located adjoining a suture pocket. A first wall segment along the suture pocket and a first sidewall segment form a contiguous surface to allow a suture needle to be slidably guided along the first wall segment and into the suture hole.

A second aspect of the present in invention is a method for attaching a suture to an implant having a suture passage according to the first aspect. The method comprises the steps of providing an implant having a suture hole disposed between a first and second suture pocket, placing a tip of a suture needle on a first pocket segment, sliding the suture needle into a first opening and pushing the suture needle through the suture hole such that the tip of the needle exits a second opening of the suture hole.

BRIEF DESCRIPTION OF THE DRAWINGS

A more complete appreciation of the subject matter of the present invention and the various advantages thereof can be realized by reference to the following detailed descriptions, in which reference is made to the accompanying drawings:

FIGS. 2A and 2B are top views of a cross section along line A-A of FIG. 1;

FIG. 2C is a side elevation view along line B-B of FIG. 2B;

FIGS. 5A and 5B are perspective views of the humeral stem of the shoulder prosthesis shown in FIG. 1;

FIG. 6A is a top view of the humeral stem of the shoulder prosthesis shown in FIG. 1;

FIG. 6B is a side elevation view of the humeral stem of the shoulder prosthesis shown in FIG. 1.

DETAILED DESCRIPTION

Figure 1:
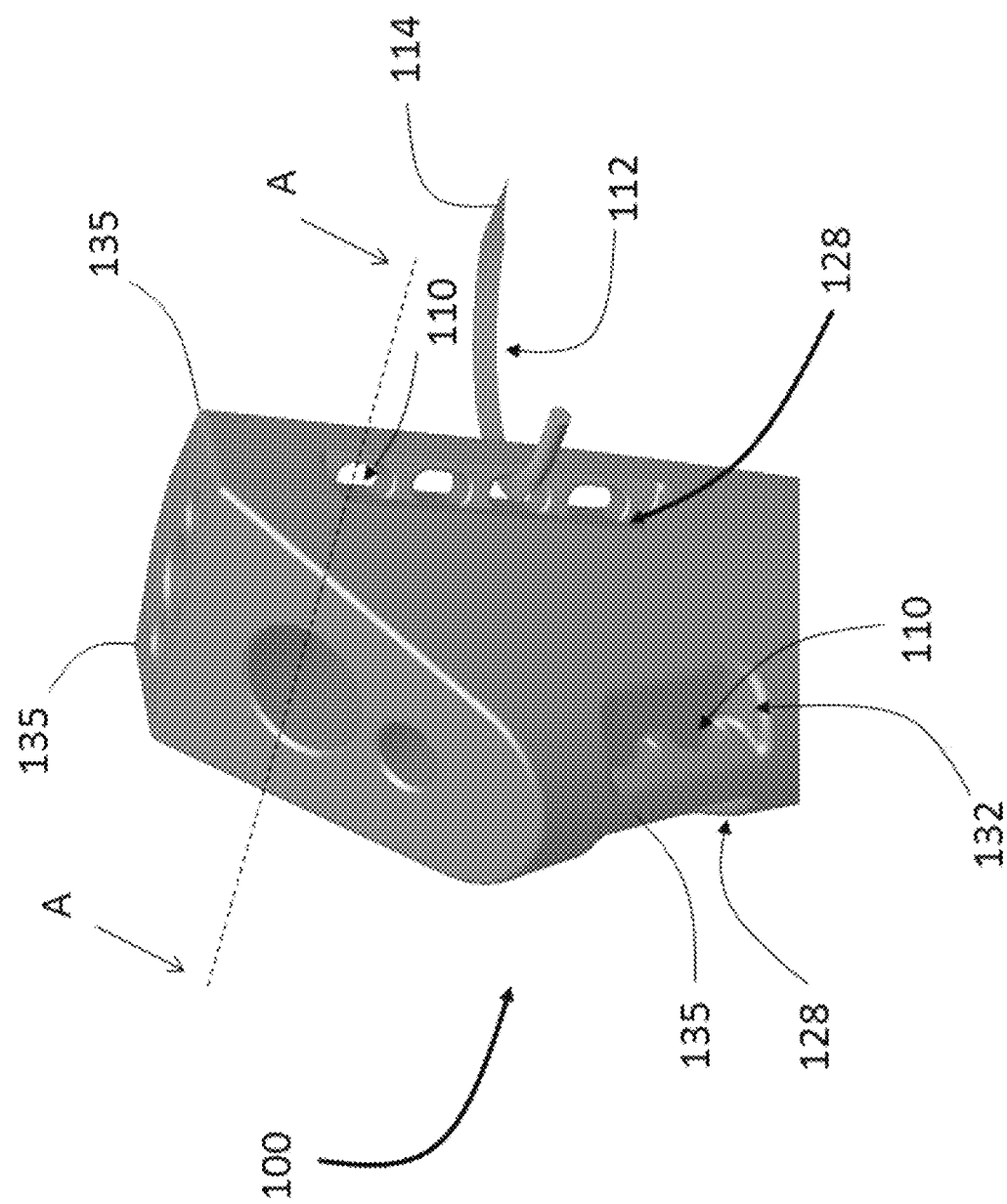
FIG. 1 is a partial perspective view of a humeral stem of a shoulder prosthesis with suture holes according to one embodiment of the present invention.

Referring to FIG. 1, there is shown a partial perspective view of humeral stem 100 having a plurality of suture holes 110 according to one embodiment of the present invention. A curved suture needle 112 with a tip 114 disposed within suture hole 110 is also shown. Suture holes 110 are disposed within a first pocket 128 and a second pocket 132. As best seen in FIG. 1, suture pockets 128 and 132 are located within the peripheral contours of humeral stem 100 forming substantially contiguous peripheral walls to facilitate soft tissue and bone manipulation during implantation of humeral stem 100.

FIGS. 2A and 2B show a cross section of suture hole 110 at line A-A. Suture hole 110 includes a first opening 116 and a second opening 118. A first sidewall 122 is made of three segments: a first pocket segment 126 in first pocket 128, a first sidewall segment 124 along suture hole 110, and a second pocket segment 130 in second pocket 132. As best seen in FIG. 2B, all three segments (124, 126, 130) of first sidewall 122 form a smooth, continuous wall free from obstructions. Consequently, needle tip 114 may be placed along first pocket segment 126 and slid smoothly across first sidewall 122 until needle tip 114 enters suture hole 110. Alternatively, needle tip 114 may be placed along second pocket segment 130 and slide smoothly in the opposite direction to enter suture hole 110 through second opening 118. Hence, first pocket segment 126 and second pocket segment 130 function as guide tracks to successfully guide a suture needle tip 114 into suture hole 110.

A second sidewall 120 is located opposite to first sidewall segment 124 and extends from first opening 116 to second opening 118 to define a first length D1. Second sidewall 120 may be chamfered at first opening 116 and at second opening 118, to facilitate suture needle entry and exit respectively.

FIG. 2C is a side elevation view along line B-B showing first pocket 128 and suture hole 110. Suture hole 110 is oblong shaped and includes a curved upper surface 134 and a curved lower surface 136 joining first sidewall segment 124 and second sidewall 120. The oblong shape and narrow shoulder area region 138 between suture holes 110 are configured to maximize insertion location points for needle tip 114. Suture needle tip 114 may be placed either directly into opening 116 or placed at any point along first pocket segment 126 and slid into opening 116 to attach a suture to humeral stem 100. Hatched region 142 shown in FIG. 2C represents all first contact locations for suture needle tip 114 whereby successful insertion of suture needle 112 may be achieved through first opening 116. Similarly, suture needle tip may also be placed at any point along second pocket segment 130, and slid into suture hole 110 through second opening 118.

Figure 3:
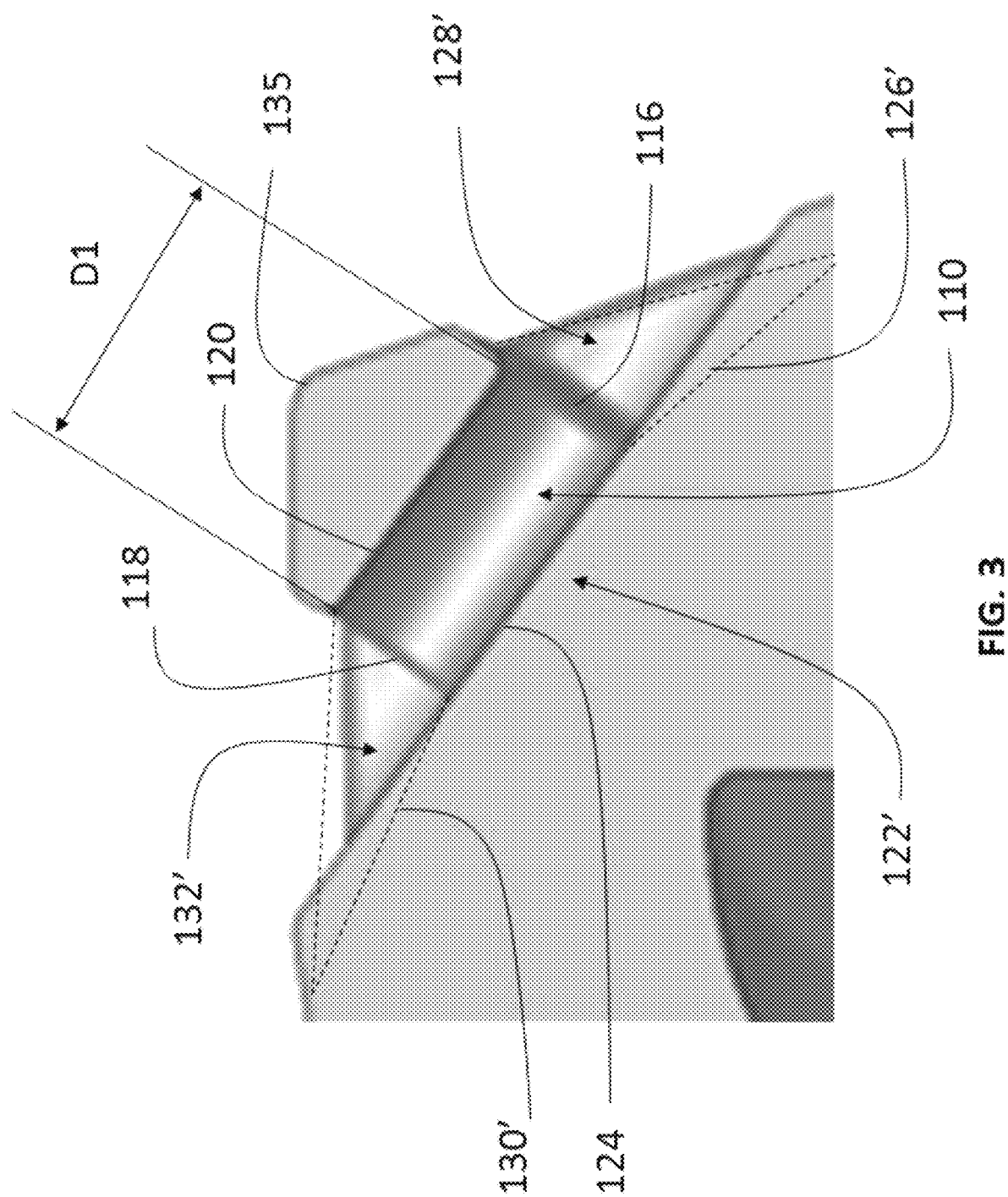
FIG. 3 is a top view of a suture hole according to another embodiment of the present invention.

FIG. 3 shows an alternate arrangement of first sidewall 122'. In this embodiment, first pocket segment 126' and second pocket segment 130' are deflected away from second sidewall 120 consequently resulting in enlarged first and second pockets 128' and 132'. These enlarged pockets provide for a wider insertion angle for tip 114, whereby needle tip 114 can be placed on first pocket segment 126' and slid readily into suture hole 110. Although first pocket segment 126' and second pocket segment 130' are angled with respect to first sidewall segment 124, first sidewall 122 provides a contiguous, uninterrupted surface that allows suture needle tip 114 to smoothly slide along first pocket segment 126' or second pocket segment 130' and into suture hole 110. First and second pocket segments 126', 130' may also be configured to deflect toward the second side wall 120 in other embodiments. In a still other embodiment, any of first pocket segment 126', first sidewall segment 124, and second pocket segment 130' may be curved and configured for specific suture needle shapes and suturing techniques.

Figure 4:
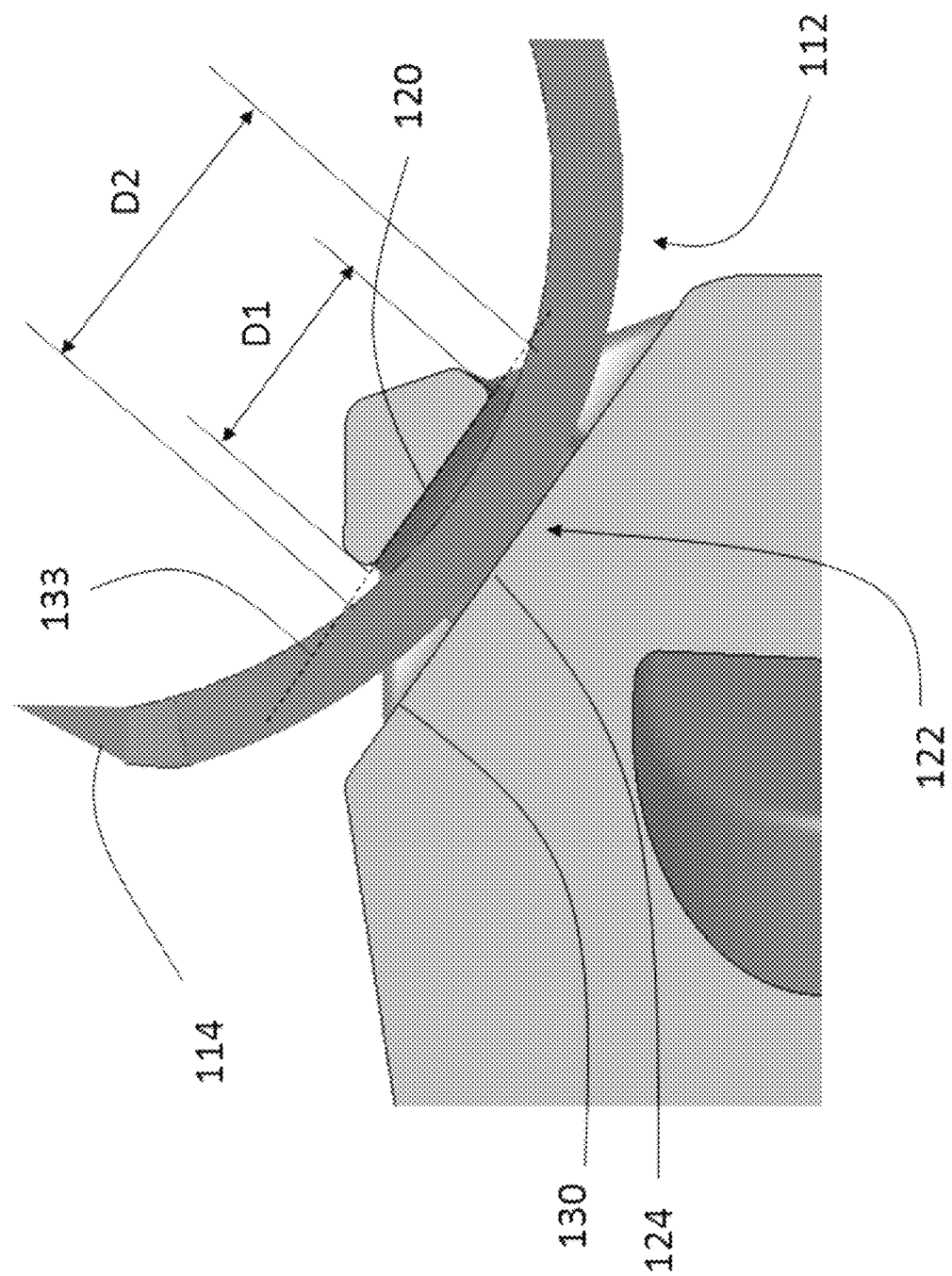
FIG. 4 is another top view of a cross section along line A-A of the suture hole including a curved suture needle.

Referring now to FIG. 4, there is shown curved suture needle 112 disposed within suture hole 110 such that needle tip 114 is outside suture hole 110. A chord length D2 of curved suture needle 112 is defined by the intersection of a plane 133 containing second sidewall 120. As best seen in FIG. 3, D2 is larger than D1. Consequently, suture needle 112 may readily pass through suture hole 110 without contacting second sidewall 120. The smooth, continuous first sidewall allows needle tip 114 to be placed on first pocket segment 126, slid into suture hole 110 and finally exit second opening 118 to complete passage of suture needle 122 through suture hole 110, without contacting second sidewall 120 as shown in FIG. 4.

FIG. 5A is a perspective view of humeral stem 100 showing a first arrangement 142 and a second arrangement 144 of suture holes 110 of the present invention. As shown in partial perspective FIG. 5B, an axis L1 running through suture hole 110 centers is offset to an axis L2 of the humeral stem 100 and proximal face 140. This offset arrangement provides a larger surface area for suture hole locations and consequently maximizes the number of suture holes 110 and suture hole area available for suture attachment.

Referring now to FIGS. 6A and 6B, there is shown a top view of proximal face 140 and a side elevation view of the proximal end of humeral stem 100 respectively. Proximal face 140 of humeral stem 100 is provided with multiple surfaces 146, 148, 150, 152, and 154. The multiple surfaces and positive slope as indicated by an axis L3 in FIG. 6B provide stability to a tuberosity during needle insertion and wrapping of sutures around tuberosity post suture insertion. The edge of humeral stem 100 is designed to be substantially squared off (not round), preventing tuberosity rotation at the corners. This design feature also provides stability for short term fixation of the tuberosity prior to bone healing. An angle 158 measured between a centerline of the humeral stem 100 and edge 135 is configured to be between 55° and 60°. This angular range for angle 158 is provided so that a surgeon may align suture pockets 128, 132 with respect to the bicipital groove by visually examining the position of edges 135 during suture insertion and wrapping of tuberosities.

Figure 7A:
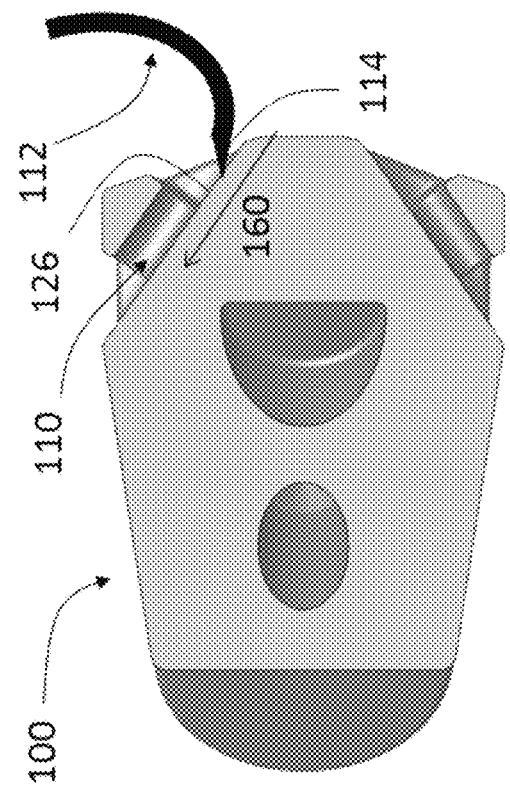
FIGS. 7A-7C are top views of the suture hole of FIG. 3 showing the sequential steps of attaching a suture to the suture hole of the present invention.
Figure 7B:
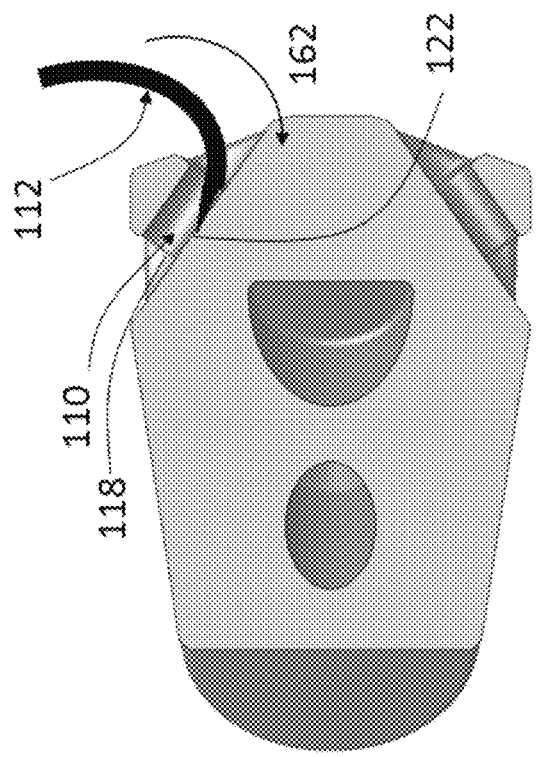
Figure 7C:
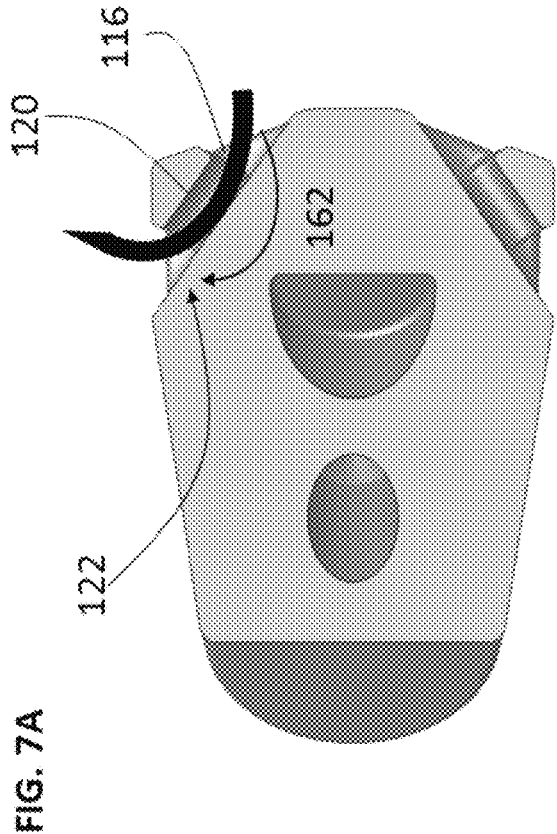

Another aspect of the present invention is a method for attaching a suture to an implant having suture holes disposed within suture pockets. Referring now to FIGS. 7A-7C, there is shown a method of inserting curved suture needle 112 to humeral stem 100 through suture hole 110. Suture needle tip 114 is placed anywhere along first pocket segment 126. Alternatively, as illustrated in FIG. 2C, suture needle tip 114 may be directly placed into first opening 116 as indicated by the hatched region 142. After contacting surgical needle tip 114 on first pocket segment 126, a surgeon may slide needle 112 in the direction of arrow 160 shown in FIG. 7A. Needle tip 114 is guided along first pocket segment 126 and into suture hole 110 as shown in FIG. 7B. As more fully explained above, seamless connection between first pocket segment 126 and first sidewall segment 124 ensures that needle tip 114 readily slides into suture hole 110. Suture needle 112 may now be rotated as indicated by arrow 162 to slide needle tip 114 from first opening 116 to second opening 118, and finally to exit suture hole 110 as shown in FIG. 7C. Thus a surgeon can readily insert suture needle 112 into suture hole 110 by placing suture needle tip 114 anywhere along the hatched region shown in FIG. 2C, and thereby minimize the effort to successfully attach sutures to an implant because successful insertion is not limited to accurately placing needle tip 114 (first point of contact) in suture hole openings. Alternatively, suture needle tip 114 may be placed along second pocket segment and slid into suture hole 110 through second opening 118. Uniform suture hole geometry will allow a surgeon to utilize a single suture insertion technique for attaching sutures to all suture holes.

While a humeral stem of a shoulder prosthesis is described in these embodiments, suture holes disclosed herein may be used with any other prostheses including, but not limited to, spinal implants with suture holes and suture anchors. Other prostheses utilizing suture holes of the present invention may have different suture holes configurations and arrangements. Suture holes may also be configured to carry multiple suture threads in a single hole. Although suture hole slots described here are oblong shaped, other shapes including, but not limited, to circular, square, rectangular, triangular, etc., may also be used.

Whereas the first sidewall 122 disclosed herein as three segments, other embodiments may only have a first sidewall with only two segments: a first pocket segment 126 and a first sidewall segment 124, i.e., with only a first pocket and no second pocket. A curved suture needle 112 is generally described here, however, the suture holes of the present invention may be used with any of, but not limited to, a straight needle, a straight needle, a half-curved needle, a curved needle and a compound curved needle. While the first sidewall and the second sidewall are generally shown to be linear here, other embodiments may have curved first and second sidewalls.

Implants containing suture holes of the present invention may be made from any of, but not limited to, PEEK, polymers and titanium and/or titanium alloys, stainless steel, and cobalt chrome. Additive manufacturing techniques such as 3D printing may be used to fabricate implants with suture holes of the present invention.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the claims below.

The invention claimed is:

1. An implant having suture pockets comprising:
a first pocket having a first planar wall segment;
a second pocket having a second planar wall segment; and
a suture hole disposed between the first and second pockets, the suture hole having a first sidewall segment extending from a first opening to a second opening, the first planar wall segment adjoining the first opening and extending away from the first opening, the second planar wall segment adjoining the second opening and extending away from the second opening,
wherein the first planar wall segment, the second planar wall segment and the first sidewall segment of the suture hole form a planar wall such that a suture needle can be slidably guided along the first and second planar wall segments and the first sidewall segment of the suture hole; and wherein a plurality of suture holes are disposed between the first and second pockets.

2. The implant of claim 1, wherein when a suture needle tip is placed on the first planar wall segment, the suture needle tip can be slidably guided across first planar wall segment and into the suture hole.

3. The implant of claim 1, wherein the suture hole includes a second sidewall segment opposite the first sidewall segment, the second sidewall segment extending from the first opening to the second opening and defining a first length.

4. The implant of claim 3, wherein the second sidewall segment is chamfered at the first opening.

5. The implant of claim 3, wherein the second sidewall segment is chamfered at the second opening.

6. The implant of claim 3, wherein a length of the suture hole measured from the first opening to the second opening is greater than a distance between the first sidewall segment and the second sidewall segment.

7. The implant of claim 1, wherein the first sidewall segment is tangential to the suture needle when the suture needle is disposed within the suture hole.

8. The implant of claim 1, wherein an upper wall and a lower wall connecting the first sidewall segment and the second sidewall segments are curved such that the suture hole is oblong shaped in a plane transverse to the first and second sidewalls.

9. The implant of claim 1, wherein the plurality of suture holes are arranged vertically below each other.

10. The implant of claim 9, wherein a vertical axis connecting the suture hole centers is offset to a vertical axis of the implant.

11. The implant of claim 1, wherein the implant is any of a shoulder or hip prostheses.

12. The implant of claim 11, wherein the first and second pockets are aligned along a bicipital groove.

13. An implant having a suture pocket comprising:

a first pocket having a first wall segment; and a suture hole adjoining the first pocket, the suture hole having a first sidewall segment extending from a first opening to a second opening, the first wall segment adjoining the first opening and extending away from the first opening;

a second pocket having a second wall segment, the second wall segment adjoining the second opening and extending away from the second opening, wherein the first wall segment and the first sidewall segment of the suture hole form a contiguous surface such that a suture needle can be slidably guided along the first wall segment and the first sidewall segment of the suture hole; and wherein a plurality of suture holes are disposed between the first and second pockets.

14. The implant of claim 13, wherein the suture hole includes a second sidewall segment opposite the first sidewall segment, the second sidewall segment extending from the first opening to the second opening and defining a first length.

15. A method of suturing an implant, comprising:

providing an implant having suture pockets with a first pocket having a first wall segment, a second pocket having a second wall segment, and a suture hole disposed between the first and second pockets, the suture hole having a first sidewall segment extending from a first opening to a second opening, the first wall segment adjoining the first opening and extending away from the first opening, the second wall segment adjoining the second opening and extending away from the second opening, wherein the first wall segment, the second wall segment and the first sidewall segment of the suture hole form a contiguous surface; wherein a plurality of suture holes are disposed between the first and second pockets placing a tip of a suture needle on the first wall segment;

sliding the suture needle into the first opening; and pushing the suture needle through the suture hole such that the tip of the suture needle exits the second opening.

16. The method of claim 15, wherein during the placing, sliding and pushing steps, the suture needle contacts only the contiguous surface.

* * * * *